(12) United States Patent
Thomson

(10) Patent No.: US 8,217,345 B2
(45) Date of Patent: Jul. 10, 2012

(54) INTERFACE BETWEEN DIFFERENTIAL MOBILITY ANALYZER AND MASS SPECTROMETER

(75) Inventor: Bruce Thomson, Toronto (CA)

(73) Assignee: DH Technologies Development Pte. Ltd., Singapore (SG)

( * ) Notice: Subject to any disclaimer, the term of this patent is extended or adjusted under 35 U.S.C. 154(b) by 524 days.

(21) Appl. No.: 12/254,244

(22) Filed: Oct. 20, 2008

(65) Prior Publication Data

US 2009/0101812 A1 Apr. 23, 2009

Related U.S. Application Data

(60) Provisional application No. 60/980,837, filed on Oct. 18, 2007.

(51) Int. Cl.
*H01J 49/00* (2006.01)

(52) U.S. Cl. .......... 250/294; 250/281; 250/282

(58) Field of Classification Search .......... 250/281, 250/282, 286, 287, 289, 294, 295, 296, 297
See application file for complete search history.

(56) References Cited

U.S. PATENT DOCUMENTS

| | | |
|---|---|---|
| 5,869,831 A | 2/1999 | De La Mora et al. |
| 5,936,242 A | 8/1999 | De La Mora et al. |
| 6,700,120 B2 | 3/2004 | Hager |
| 6,787,763 B2 | 9/2004 | De La Mora et al. |
| 6,906,322 B2 * | 6/2005 | Berggren et al. ............ 250/288 |
| 2006/0186334 A1 * | 8/2006 | Jolliffe et al. ................ 250/288 |
| 2006/0226353 A1 * | 10/2006 | Tang et al. .................... 250/287 |
| 2006/0237669 A1 * | 10/2006 | Miller et al. ............... 250/504 R |

OTHER PUBLICATIONS

S. Ude et al. "Charge-Induced Unfolding of Multiply Charged Polyethylene Glycol Ions", J. Am. Chem. Soc. 2004, 126, pp. 12184-12190.

Juan Fernandez de la Mora et al., "The potential of diferential mobility analysis coupled to MS for the study of very large singly and multiply charged proteins and protein complexes in the gas phase", Biotechnol. J. 2006, 1, pp. 1-10, Wiley-VCH Verlag GmbH & Co.

Juan Fernandez de la Mora et al., Tandem Mobility Mass Spectrometry Study of Electrosprayed Tetraheptyl Ammonium Bromide Clusters, J. Am. Soc. Mass. Spectrom 2005, 16, pp. 717-732, Elsevier Inc.

* cited by examiner

*Primary Examiner* — Michael Maskell
*Assistant Examiner* — Hanway Chang

(57) ABSTRACT

Various embodiments are described herein for an apparatus that can be used to interface a Differential Mobility Analyzer (DMA) with a Mass Spectrometer (MS). The apparatus includes first and second plates with first and second apertures respectively, and an interface region in between the first and second plates. During use, the first aperture receives mobility separated ions from the DMA, the interface region receives a gas flow to prevent gas outflow from the DMA toward the MS, and the first and second plates are configured to receive voltages to generate an electric field there between to guide the mobility separated ions from the first aperture to the second aperture, which then provides the mobility separated ions to the MS.

25 Claims, 2 Drawing Sheets

INTERFACE BETWEEN DIFFERENTIAL MOBILITY ANALYZER AND MASS SPECTROMETER

CROSS REFERENCES TO RELATED APPLICATIONS

This application claims the benefit of U.S. Provisional Application No. 60/980,837 filed Oct. 18, 2007, and the entire contents of which are hereby incorporated by reference.

FIELD

The various embodiments described herein generally relate to interfacing a mobility analysis device with an ion analysis device.

INTRODUCTION

An ion mobility analyzer is designed to separate ions based on ion mobility, and can separate ions that have different shapes or collision cross-sections. Accordingly, ion mobility can also be used to measure the collision cross-section of an ion in order to provide information about the shape of an ion. Since a Mass Spectrometer (MS) is designed to filter ions based on mass-to-charge ratio, the analysis results of a complex mixture can be enhanced when an ion mobility analyzer is combined with a MS. This is because the combination of the ion mobility analyzer and the MS can separate species that have the same mass-to-charge ratio but different shape as well as species that have the same mass-to-charge ratio but different charge. Both of these operations can reduce chemical noise interference and increase signal-to-noise ratio.

Ion mobility analyzers generally use an electric field to drift ions through a gas in a drift region. The speed of the ion is related to the electric field by:

$$v = K \cdot E \quad (1)$$

where v is ion velocity in units of m/s, E is electric field strength in the drift region in units of V/m and K is ion mobility in units of $m^2/(V \cdot s)$. One method of separating ions by mobility is to provide a pulse of ions into the drift region and measure the flight time over a fixed distance. This requires creating a pulse of ions, which involves either wasting ions from a continuous beam or trapping them in front of pulsing regions.

Another method of separating ions by mobility is employed by a Differential Mobility Analyzer (DMA), which separates ions in space rather than in time. Ions are continuously introduced through an entrance aperture in a DMA entrance plate and then drift across a DMA drift region, which is a fixed enclosed space, to an exit aperture in a DMA exit plate. An electric field is applied between the DMA entrance plate and the DMA exit plate, i.e. across the DMA drift region. A sheath gas flow is also introduced into the DMA drift region, which is generally maintained at atmospheric pressure. The direction of the sheath gas flow is transverse with respect to the direction of the flow of ions such that the ions in the DMA drift region flow in a direction that is approximately perpendicular to the sheath gas flow. The faster ions reach the DMA exit plate upstream of the slower ions. A narrow DMA electrode near the DMA exit plate measures the ion current. By varying the electric field strength across the DMA drift region, ions of different mobility are swept across the DMA electrode to register an ion mobility spectrum.

The best separation efficiency (i.e. mass resolution) results when the electric field strength within the DMA drift region is very high and the width of the DMA drift region is small, so that the diffusion of the ions is minimized. This in turn requires a very high gas flow velocity under laminar flow conditions for the sheath gas flow. Flow characteristics can be characterized by the Reynolds number (Re), which is widely used in fluid mechanics, and is characterized in equation 2.

$$Re = (\rho \cdot v \cdot D)/\mu \quad (2)$$

In equation 2, the variable $\rho$ is the gas density in $g/cm^3$, v is the gas velocity in cm/s, D is the characteristic dimension of the chamber in cm and $\mu$ is the kinematic viscosity of the gas in g/cm-sec. Gas flow becomes turbulent above a Reynolds number of 2,000. In a properly designed DMA, the laminar flow can be maintained for some distance at a Reynolds number approaching 100,000 if no flow disturbances are introduced and the walls defining the DMA drift region are smooth.

In current implementations that combine a DMA with a MS, ions are directly sampled from the exit aperture of the DMA into the vacuum region of the MS. In some cases, the DMA exit plate can also serve as the inlet plate of the MS. At a fixed electric field strength within the DMA drift region, only the ions of a particular mobility will be transmitted to the MS.

SUMMARY

In one aspect, at least one embodiment described herein provides a method of providing an interface between a DMA and a MS. The method comprises providing a first plate with a first aperture configured to receive mobility separated ions from the DMA during use; providing a second plate with a second aperture configured to provide the mobility separated ions to the MS during use; providing an interface region in between the first and second plates, the interface region being configured to receive a gas flow during use to reduce sheath gas outflow from the DMA toward the MS; and configuring the first and second plates to receive voltages during use to generate an electric field there between to guide the mobility separated ions from the first aperture to the second aperture.

In another aspect, at least one embodiment described herein provides an apparatus for interfacing a DMA with a MS. The apparatus comprises a first plate with a first aperture configured to receive mobility separated ions from the DMA during use; a second plate with a second aperture configured to provide the mobility separated ions to the MS during use; and an interface region in between the first and second plates, the interface region being configured to receive a gas flow during use to reduce gas outflow from the DMA toward the MS. The first and second plates are configured to receive voltages during use to generate an electric field there between to guide the mobility-separated ions from the first aperture to the second aperture.

Further aspects and features of the embodiments described herein will appear from the following description taken together with the accompanying drawings.

BRIEF DESCRIPTION OF THE DRAWINGS

The skilled person in the art will understand that the drawings, described below, are for illustration purposes only. The drawings are not intended to limit the scope of the applicant's teachings in any way. For a better understanding of the embodiments described herein, and to show more clearly how the various embodiments described herein may be carried into effect, reference will be made, by way of example, to the drawings in which.

DESCRIPTION OF THE VARIOUS EMBODIMENTS

Figure 1:
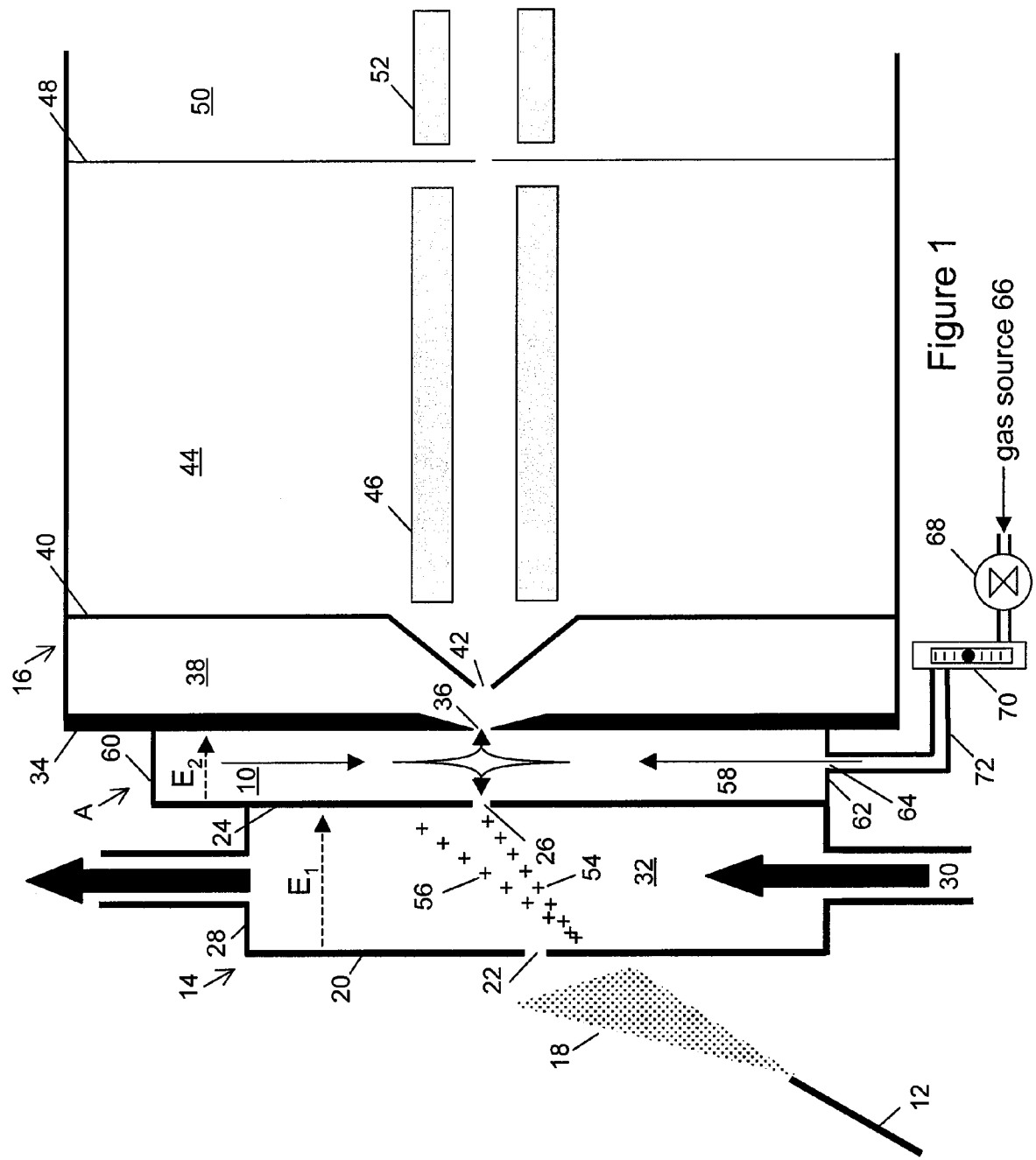
FIG. 1 is a schematic illustration of an exemplary embodiment of a portion of an apparatus that includes an interface region that can be used to combine a DMA with a MS.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description of the various examples provided herein is meant to further an understanding of various aspects of the applicant's teachings and should not be construed as limiting the scope of the present teachings in any way.

Referring now to FIG. 1, shown therein is a schematic illustration of an exemplary embodiment of a portion of an apparatus A that includes an interface region 10 that can be used to combine a Differential Mobility Analyzer (DMA) with a Mass Spectrometer (MS). Portions of an ion source 12, a DMA 14 and a MS 16 are also shown in FIG. 1. The interface region 10 in effect provides a buffer between the DMA 14 and the MS 16, which allows values for certain parameters of each of these devices to be selected independently of one another. Accordingly, the interface region 10 allows these devices to operate in a somewhat more independent fashion, which makes the combination of these devices provide more effective results.

The ion source 12 generates a plurality of sample ions 18 from a sample. Examples of the ion source 12 include, but are not limited to, an electrospray ion source, an Atmospheric Pressure Chemical Ionization (APCI) ion source, an atmospheric pressure Matrix Assisted Laser Desorption Ionization ion source (MALDI), an Atmospheric Pressure PhotoIonization (APPI) ion source, a Desorption ElectroSpray Ionization (DESI) ion source, and the like.

The DMA 14 comprises a DMA entrance plate 20 with an entrance aperture 22, and a DMA exit plate 24 with an exit aperture 26. The entrance and exit apertures 22 and 26 can be formed as slits in the DMA entrance and exit plates 20 and 24 respectively. It should be understood that the DMA 14 generally comprises an enclosed chamber, save for the elements required for creating and re-circulating a sheath gas flow, and FIG. 1 only shows a side view of a portion of the chamber, which also includes a top wall 28, and a bottom and two side walls (not shown) that connect to the DMA entrance and exit plates 20 and 24 to form an enclosed space. Also shown are portions of a loop for circulating a gas through the DMA 14 which is described in more detail below.

The DMA 14 also includes a gas assembly and a sheath gas generation element (both elements not shown) for generating a sheath gas flow 30 within the DMA drift region 32. The sheath gas generation element consists of a high capacity air pump or blower that circulates the sheath gas and directs the gas flow through the DMA drift region. The gas assembly includes a gas source and a piping assembly (both not shown) to form a continuous flow of gas through the DMA 14 typically in the range of 10 to 100 L/s. The DMA drift region 32 is generally maintained at atmospheric pressure. If the exit aperture 26 is formed as a slit, the major axis of the slit (i.e. its length) is typically oriented perpendicular to the direction of the sheath gas flow 30.

The DMA entrance and exit plates 20 and 24 are also configured to receive voltages during use for setting up an electric field $E_1$ across the DMA drift region 32. Accordingly, these elements include contacts (not shown) that connect to a voltage source as is commonly known by those skilled in the art. The direction of the electric field $E_1$ is generally perpendicular to the direction of the sheath gas flow 26. Conventional power supplies can be used as is commonly known by those skilled by the art and hence are not shown.

The MS 16 includes an orifice plate 34 with an inlet aperture 36, a first vacuum region 38, a skimmer plate 40 with a conical orifice 42, a second vacuum chamber 44 and a first multipole rod set 46. The MS 16 also includes a plate 48, a third vacuum chamber 50 and a second multipole rod set 52. The first vacuum region 38 can be a differentially pumped vacuum chamber that has a pressure of approximately 0.133 kPa and the second vacuum chamber 44 is evacuated to a lower pressure at approximately 0.00133 kPa. The third vacuum chamber 50 is typically at an even lower pressure at approximately $1.3 \times 10^{-6}$ kPa. The first multipole rod set 46 is typically an RF ion guide and the second multipole rod set 52 can receive DC and RF voltages and provide mass resolving functionality. Conventional power supplies, and pumps, including roughing pumps and turbo pumps, can be used as is commonly known by those skilled by the art and hence not shown. Other configurations and pressures can be used for the MS 16 as is commonly known by those skilled in the art. For example, the MS 16 can be, but is not limited to, a quadrupole MS, a triple quadrupole MS, an ion trap MS, a Quadrupole-quadrupole Time Of Flight (QqTOF) MS, a Fourier Transform MS, a magnetic sector MS and the like.

In use, the sample ions 18 are generated by the ion source 12 and directed towards the aperture 22 in the DMA entrance plate 20. Once the sample ions 18 are inside the DMA drift region, they are subjected to the sheath gas flow 26 and the electric field $E_1$. This separates the sample ions 18 into mobility separated ions including higher mobility sample ions 54 and lower mobility sample ions 56 as is known by those skilled in the art. The lower mobility sample ions 56 are directed too far upwards by the sheath gas flow 30 and cannot exit through the exit aperture 26. However, the higher mobility sample ions 54 are displaced upwards by the correct amount by the sheath gas flow 30 so that these ions can exit through the exit aperture 26. During operation, the voltages that set up the electric field $E_1$ and the velocity of the sheath gas flow 30 can be selected such that sample ions 54 having a desired mobility can exit through the exit aperture 26 while the other sample ions 56 hit the exit plate 24.

Figure 2:
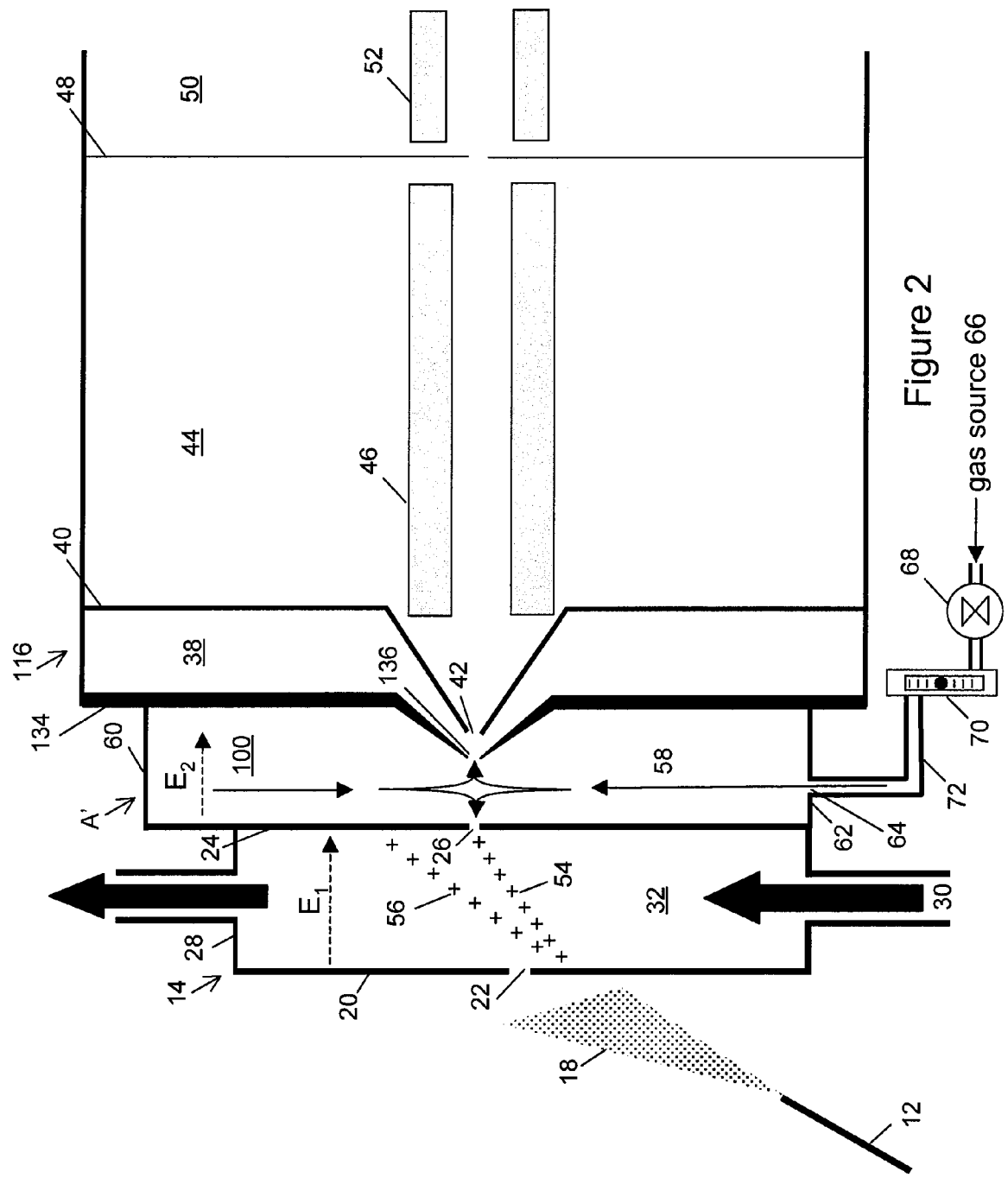
FIG. 2 is a schematic illustration of another exemplary embodiment of a portion of an apparatus that includes an interface region that can be used to combine a DMA with a MS.

If the interface region 10 were not present, the mobility separated ions that exit the exit aperture 26 travel to the inlet aperture 36 of the orifice plate 34 into the MS 16. These ions would then enter the second vacuum chamber 44 and typically be cooled and focused by the multipole rod set 46. The first vacuum region 38 typically acts as an interface between the second vacuum region 44 and regions upstream from the first vacuum region that are typically around atmospheric pressure. Accordingly, the first vacuum region 38 serves to remove gas from the ion stream, before further processing in the MS 16. The ions then pass into the third vacuum chamber 50 for further processing depending on the particular structure of the MS 16 as is commonly known by those skilled in the art. The structure of the MS 16 shown in FIGS. 1 and 2 is for exemplary purposes only and other types of structures can be used for the MS 16.

In a properly designed DMA, the sheath gas flow 26 can be laminar for some distance at a Reynolds number approaching 100,000 if there are no flow disturbances and the walls defining the DMA drift region 32 are smooth. Accordingly, any outflow of gas from the DMA drift region 32 can disturb the laminar sheath gas flow 30 and the steady state pressure condition within the DMA drift region 32. This can affect the ion motion in the region of the outflow, causing a loss of ion mobility resolution for the DMA 14. Outflow of gas from the DMA drift region 32 can occur at both the exit and entrance apertures 26 and 22.

In addition, the gas through which the sample ions travel in the DMA drift region 32 is typically kept as pure and clean as possible to minimize reactions and clustering that complicate the spectrum and reduce the signal. In a DMA with a drift region having a 0.5 cm width, achieving a Re number greater than 20,000 can require a gas flow of up to 2,800 L/min. Since pure gas cannot be supplied at that rate, the drift or sheath gas is re-circulated after purifying by introducing clean gas into a closed loop (a portion of which is shown) as is known by those skilled in the art.

However, leaks must be reduced in the DMA 14. Accordingly, the interface region 10 is used to couple the DMA 14 to the MS 16. The interface region 10 compensates or reduces any outward leak of the sheath gas into the MS 16. If the interface region 10 is not used, sample ions and sheath gas are drawn from the exit aperture 26 of the DMA 14 into the first vacuum region 38 of the MS 16. This suctioning process can draw sample ions and sheath gas from a wider region of the DMA 14 than is defined by the width of the ion beam for a particular ion mobility; this is especially true for a high-sensitivity MS that uses a large size for the inlet aperture 32. Typically, the ions can be pulled from a region that is twice the diameter of the aperture due to this vacuum suction, although this depends on the strength of the electric field $E_1$ across the DMA drift region 32. Drawing the ions from a wider region than the exit aperture 26 can adversely affect the ion mobility separation process and reduce the effective ion mobility resolution provided by the DMA 14.

The interface region 10 includes a first plate with a first aperture configured to receive mobility-separated ions from the DMA 14 during use. The interface region 10 also includes a second plate with a second aperture configured to provide the mobility-separated ions to the MS 16 during use. The interface region 10 also receives a gas flow 58 during use to prevent outflow of the sheath gas 30 from the DMA 14 towards the MS 16. The first and second plates of the interface region 10 are also adapted to receive voltages, i.e. electrical contacts (not shown) can be used, during use to generate an electric field $E_2$ in the interface region 10 to guide the mobility separated ions from the first aperture to the second aperture. It should be understood that the interface region 10 is generally an enclosed chamber, with several apertures, and includes top and bottom walls 60 and 62, and side walls (not shown) that are connected to the first and second plates and the top and bottom walls 60 and 62. The interface region 10 can have a gap of 2 to 4 mm, which is generally enough to prevent electric breakdown between the DMA 14 and the inlet of the MS 16, and small enough to allow good ion transmission between the DMA 14 and the MS 16.

The interface region 10 is connected to a pump assembly that is connected to a gas source 66 to receive the gas flow 58 through an aperture 64. The pump assembly includes a pump (not shown), a valve 68, an adjustable flow meter 70, and a piping assembly 72. Alternatively, a pressurized gas supply, such as a cylinder, can be used as the gas source 66 and the pump. The gas flow 58 can be introduced from various locations into the interface region 10, where it will fill up the interface region 10 and exit into the first vacuum region 38 and into the DMA drift region 32 as shown by the arrows in FIG. 1 (the dashed arrows in FIG. 1 signify the direction of an electric field and the solid arrows signify the direction of gas flow). The gas source 66 provides a supply of clean gas such as argon, nitrogen or another inert gas. Typical flow rates for the gas flow 58 can be in the range of 0.5 to 10 L/min. Typical gas flow into the first vacuum region 38 can be about 0.5 L/min, so the flow rate of the gas flow 58 equals or exceeds this value.

The gas flow 58 is adjusted to create a pressure within the interface region 10 that can be approximately equal to or greater than the pressure within the DMA drift region 32. The gas flow 58 is also at least approximately equal to or greater than the gas suction flow into the MS 16. This ensures that the gas flow into the MS 16 is provided by the gas flow 58 rather than from the DMA sheath gas flow 30 so that the flow into the first vacuum region 38 does not disturb the laminar sheath gas flow 30 within the DMA drift region 32. Accordingly, the gas flow 58 within the interface region 10 reduces the amount of gas that the MS 16 suctions from the sheath gas flow 30 of the DMA 14. In at least some cases, the amount of the gas flow 58 can be configured to prevent the any of the sheath gas flow 30 from entering into the MS 16 or the interface region 10. The gas flow into the first vacuum region 38 is determined by the size of the inlet aperture 36, and so the amount of the gas flow 58 can be calculated to be larger than the gas flow into the first vacuum region 38 in at least some cases. Adding more than this amount will result in the excess gas flow going into the DMA 14.

The gas flow 58 can be controlled by using the flow meter 68, and adjusted to provide enough flow to reduce the outflow of sheath gas flow 30 from the DMA 14 into the interface region 10, to have flow of gas between the DMA 14 and the interface region 10, or to have an excess gas flow that will go from the interface region 10 into the DMA 14. Adjustment of the gas flow 58 can also be done to maximize the sensitivity and resolution of the DMA 14. However, if the gas flow 58 is too high, the mobility-separated ions will be blown away and prevented from entering the interface region 10 thereby reducing sensitivity and potentially disturbing the sheath gas flow 30 in the DMA 14, reducing DMA resolution. Accordingly, when the gas flow 58 is adjusted to provide a small counter flow into the DMA drift region 32, this is controlled to provide minimal disturbance to the sheath gas flow 30.

The electric field $E_2$ in the interface region 10, between the DMA 14 and the inlet aperture 36 of the MS 16, will guide mobility-separated ions from the exit aperture 26 of the DMA 14 across the interface region 10 towards the inlet aperture 36 where they enter the first vacuum region 38. Accordingly, the use of the electric field $E_2$, rather than gas suction, to transmit these ions to the MS 16 allows the laminar sheath gas flow 30 in the DMA drift region 14 to not be disturbed. The strength of the electric field $E_2$ can be adjusted to achieve a desired amount of ion focusing of the mobility-separated ions in the interface region 10. This can provide high or increased ion transmission through the interface region 10. In alternative embodiments, the electric field $E_2$ can also be made strong enough, if desired, to penetrate within the DMA 14 to focus the mobility separated ions toward the exit aperture 26. However, if the electric field $E_2$ is made too strong, this will also reduce the mobility resolution of the DMA 14.

Typical voltages that can be used for the combination of the DMA 14, interface region 10 and the MS 16, include applying X Volts to the orifice plate 34, X+300 volts to the first plate of the interface region 10 (which happens to also be the DMA exit plate 24 in this exemplary embodiment), and X+300+Y on the DMA entrance plate 22, where Y is the DMA voltage. The voltage X can be in the range of 30 to 110 Volts, which is adjusted to maximize transmission and ion de-clustering in the orifice/skimmer region of the MS 16 as is commonly known by those skilled in the art. The voltage Y can be in the range of 1000 to 5000 Volts, which is scanned or adjusted to transmit sample ions having a particular ion mobility as is commonly known by those skilled in the art. These are typical voltages but other voltages can also be used. These voltages generally depend to some degree on the spacing between the DMA exit plate 24 and the orifice plate 34 of the MS 16. These voltages can be further adjusted by observing performance and maximizing ion transmission to the MS 16 as is known by those skilled in the art.

The use of an interface region 10 allows different sizes to be used for the exit aperture 26 and the inlet aperture 36. Accordingly, a large size can be used for the inlet aperture 36 into the MS 16, such as that used for high-sensitivity MS systems. If the interface region 10 were not used, then the use of a large-size inlet aperture would produce a large gas outflow from the DMA 14, causing sample ions to be pulled from a larger region from the DMA 14, thus reducing the resolution. Also, a narrow size can be used for the exit aperture 26 of the DMA 14 in order to maintain the resolution of the DMA, independent from the size of the inlet aperture 36 into the MS 16.

The use of the interface region 10 also allows for the gas composition in the DMA drift region 28 to be controlled independently from the composition of the gas that is sampled into the MS 16. This allows for ion mobility measurements in different types of gas. For example, the gas composition in the DMA 14 can be controlled by adding other gas mixtures at low concentrations into the DMA sheath gas flow 30. One way to achieve this is to put a liquid in a tee and flow gas over it, to mix the vapors together in the headspace. Another way to achieve this can be to add gas from a cylinder. For example, adding solvent vapors like ethanol or methanol can affect the DMA separation process and result in better separation of ion mobility.

The use of the interface region 10 also allows for independently controlling the amount of humidity in the DMA drift region 28 and the interface region 10. For example, the gas in the interface region 10 is typically a pure clean, dry gas (usually nitrogen), because it enters the first vacuum region 38 of the MS 16.

The apparatus shown in FIG. 1 can be manufactured in various ways. For instance, the interface region 10, the ion source 12, the DMA 14, and the MS 16 can be manufactured as separate units. The pump assemblies can also be constructed as separate units. These separate units are then connected together and the pump assemblies are connected using hoses as is known by those skilled in the art. Alternatively, the interface region 10 and the DMA 14 can be constructed as a single unit. In this case, the DMA exit plate 24 and the DMA exit aperture 26 provide the first plate and the first aperture respectively of the interface region 10. In this case, the DMA 14 and the interface region 10 can be removed so that the MS 16 can be operated with the ion source 12 without using ion mobility differentiation. In another alternative, the interface region 10 and the MS 16 can be constructed as a single unit. In this case, the MS entrance plate (i.e. orifice plate 34) and the MS entrance aperture (i.e. inlet aperture 36) provide the second plate and the second aperture respectively of the interface region 10. In yet another alternative, the interface region 10, the DMA 14 and the MS 16 can be manufactured as one unit in which case some of the components of the DMA 14 and the MS 16 provide some of the components of the interface region 10 as just described.

Referring now to FIG. 2, shown therein is a schematic illustration of another exemplary embodiment of a portion of an apparatus A' that includes an interface region 100 that can be used to combine the DMA 14 with a MS 116. In this case, the MS 116 includes an orifice plate 134 with a conical-shaped inlet aperture 136. Interfacing such a MS with the DMA 14 is not possible since the DMA 14 requires a flat surface for the DMA exit plate 24. Accordingly, the use of the interface region 100 allows for the use of a conical interface as the entrance plate of the MS 116 without disturbing the laminar sheath gas flow 30 in the DMA 14 or changing the geometry of the conical-shaped inlet aperture 136.

The conical-shaped inlet aperture 136 provides better ion focusing and improves ion sampling efficiency into the MS 116 since the incoming ions are focused towards the sharp tips of the aperture 136. This allows high sensitivity and mobility resolution to be achieved simultaneously. In alternative embodiments, the MS can include a tube rather than a conical interface, which can still be accommodated by the interface region 10 without having a detrimental effect on the operation of the DMA 14. The embodiment shown in FIG. 2 can be manufactured using the different techniques that were described for the embodiment of FIG. 1.

Typically, the entrance aperture 22 of the DMA 14 is a slit that is 20 mm long by 0.2 to 0.5 mm wide, and the exit aperture 26 of the DMA 14 is a slit that is 20 mm long by 0.2 to 0.5 mm wide. The strength of the electric field $E_2$ in the interface region is typically equal to or greater than the strength of the electric field $E_1$ in the in the DMA drift region 32. The gas flow 58 in the interface region can be selected to be slightly greater than the gas flow into the first vacuum region 38. The gas flow into the first vacuum region 38 can be calculated or measured. For example, a circular aperture of diameter 0.25 mm for the aperture 36 results in a gas flow of 0.58 L/min into the first vacuum region 38, so the gas flow 58 can be selected to be slightly larger such as 0.7 L/min for example. However, as stated above the amount of the gas flow 58 can be adjusted empirically and values other than those given in this paragraph can be used in alternative implementations of the embodiments described herein.

While the applicant's teachings are described in conjunction with various embodiments, it is not intended that the applicant's teachings be limited to such embodiments. On the contrary, the applicant's teachings encompass various alternatives, modifications and equivalents, as will be appreciated by those of skill in the art, the general scope of which is defined in the appended claims.

The invention claimed is:

1. A method of providing an interface between a Differential Mobility Analyzer (DMA) and a Mass Spectrometer (MS), wherein the method comprises:
    providing a first plate with a first aperture configured to receive mobility separated ions from the DMA during use;
    providing a second plate with a second aperture configured to provide the mobility separated ions to the MS during use;

providing an interface region in between the first and second plates, the interface region being configured to receive a gas flow during use to reduce sheath gas outflow from the DMA toward the MS; and configuring the first and second plates to receive voltages during use to generate an electric field there between to guide the mobility separated ions from the first aperture to the second aperture, wherein the gas flow received into the interface region is adjusted to create a pressure within the interface region that is approximately equal to or greater than a pressure within the DMA.

2. The method of claim 1, wherein the gas flow received into the interface region is equal to or greater than the gas flow into the MS, whereby the sheath gas outflow from the DMA into the MS is eliminated.

3. The method of claim 2, wherein the method further comprises providing a second gas source to the DMA to provide a second gas flow used to set up the sheath gas flow in the DMA and to independently control gas composition in a drift region of the DMA and the interface region.

4. The method of claim 3, wherein the gas flow received into the interface region is adjusted to cause gas to flow from the interface region into the DMA drift region.

5. The method of claim 4, wherein the gas flow received into the interface region is adjusted to be at least between 0.5 L/min and 10 L/min.

6. The method of claim 1, wherein the method further comprises providing the voltages with amplitudes to adjust electric field strength within the interface region to provide additional ion focusing in the interface region.

7. The method of claim 1, wherein the method further comprises providing the voltages with amplitudes to increase electric field strength within the interface region to penetrate within the DMA to focus the mobility separated ions toward the first aperture.

8. The method of claim 1, wherein the method further comprises providing the first and second apertures with different sizes.

9. The method of claim 1, wherein the method further comprises using a DMA exit plate and a DMA exit aperture as the first plate and the first aperture respectively.

10. The method of claim 1, wherein the method further comprises using a MS entrance plate and a MS entrance aperture as the second plate and second aperture respectively.

11. The method of claim 1, wherein the method further comprises providing a conical interface as the MS entrance plate.

12. The method of claim 1, wherein the method further comprises providing the gas flow to the interface region to prevent gas flow from the DMA to the MS during use.

13. An apparatus for interfacing a Differential Mobility Analyzer (DMA) with a Mass Spectrometer (MS), wherein the apparatus comprises:

a first plate with a first aperture configured to receive mobility separated ions from the DMA during use;

a second plate with a second aperture configured to provide the mobility separated ions to the MS during use, the first and the second plate configured to receive voltages during use to generate an electric field therebetween to guide the mobility separated ions from the first aperture to the second aperture; and an interface region in between the first and second plates, the interface region being configured to receive a gas flow during use to reduce gas outflow from the DMA toward the MS, wherein, the gas flow received into the interface region is adjusted to create a pressure within the interface region that is equal to or greater than a pressure within the DMA.

14. The apparatus of claim 13, wherein the apparatus further comprises a first gas source configured to provide the gas flow to the interface region to reduce gas flow from the DMA to the MS during use.

15. The apparatus of claim 14, wherein the apparatus further comprises a second gas source configured to provide a second gas flow used to set up the sheath gas flow in the DMA and to independently control gas composition in a drift region of the DMA and the interface region.

16. The apparatus of claim 13, wherein, in use, the voltages are configured with amplitudes to adjust electric field strength within the interface region to provide additional ion focusing in the interface region.

17. The apparatus of claim 13, wherein, in use, the voltages are configured with amplitudes to increase electric field strength within the interface region to penetrate within the DMA to focus the mobility separated ions toward the first aperture.

18. The apparatus of claim 13, wherein the first and second apertures have different sizes.

19. The apparatus of claim 13, wherein the first plate and the first aperture are a DMA exit plate and a DMA exit aperture, respectively.

20. The apparatus of claim 13, wherein the second plate and the second aperture are an MS entrance plate and an MS entrance, respectively.

21. The apparatus of claim 20, wherein the MS entrance plate comprises a conical interface.

22. The apparatus of claim 13, wherein the gas flow is provided to the interface region to prevent gas flow from the DMA to the MS during use.

23. The apparatus of claim 13, wherein the gas flow received into the interface region is equal to or greater than the gas flow into the MS, whereby the sheath gas outflow from the DMA into the MS is eliminated.

24. The apparatus of claim 13, wherein the gas flow into the interface region is adjusted to cause gas to flow from the interface region into the DMA drift region.

25. The apparatus of claim 24, wherein the gas flow received into the interface region is adjusted to be at least between 0.5 L/min and 10 L/min.

* * * * *